United States Patent
Kim et al.

(10) Patent No.: US 10,443,090 B2
(45) Date of Patent: Oct. 15, 2019

(54) METHOD AND APPARATUS FOR DETECTING TRANSLOCATION

(71) Applicant: ELECTRONICS AND TELECOMMUNICATIONS RESEARCH INSTITUTE, Daejeon (KR)

(72) Inventors: Min-Ho Kim, Daejeon (KR); Dae-Hee Kim, Daejeon (KR); Ho-Youl Jung, Daejeon (KR); Young-Won Kim, Daejeon (KR); Myung-Eun Lim, Daejeon (KR); Jae-Hun Choi, Daejeon (KR); Young-Woong Han, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 911 days.

(21) Appl. No.: 14/949,813

(22) Filed: Nov. 23, 2015

(65) Prior Publication Data
US 2016/0145680 A1    May 26, 2016

(30) Foreign Application Priority Data

Nov. 25, 2014 (KR) ......... 10-2014-0165379
Jul. 31, 2015 (KR) ......... 10-2015-0108842

(51) Int. Cl.
*G16B 20/00* (2019.01)
*G16B 30/00* (2019.01)
*C12Q 1/6827* (2018.01)
*C12Q 1/6816* (2018.01)

(52) U.S. Cl.
CPC ......... *C12Q 1/6827* (2013.01); *C12Q 1/6816* (2013.01); *G16B 20/00* (2019.02); *G16B 30/00* (2019.02)

(58) Field of Classification Search
CPC ......... G06F 19/22; G16B 20/00; G16B 20/10; G16B 30/00–20
See application file for complete search history.

(56) References Cited

U.S. PATENT DOCUMENTS 7,948,564 B2    5/2011 Jung et al.
2013/0158885 A1    6/2013 Park

FOREIGN PATENT DOCUMENTS

KR    10-2010-0097139 A    9/2010
KR    10-2014-0061223 A    5/2014
WO    WO 2009/062166 A2    5/2009

OTHER PUBLICATIONS

Li et al. The sequence Alignment/Map format and SAMtools. Bioinformatics, vol. 25, No. 16, pp. 2078-2079, 2009. (Year: 2009).*
Rausch et al. Delly: structural variant discovery by integrated paired-end and split-read analysis. Bioinformatics, vol. 28, pp. i333-i339, Sep. 15, 2012. (Year: 2012).*
Koboldt et al. Chapter 18: "Massively parallel sequencing approaches for characterization of structural variation" in Genomic Structural Variants: Methods and Protocols, Methods in Molecular Biology, vol. 838, Lars Feuk (ed.), pp. 369-384, 2012. (Year: 2012).*
Zhang et al. Identification of genomic indels and structural variations using split reads. BMC Genomics, vol. 12, 375, 2011, printed as p. 1/12-12/12. (Year: 2011).*
Stoll, C. Nonrandom distribution of exchange points in patients with reciprocal translocations. Human Genetics, vol. 56, pp. 89-93, 1980. (Year: 1980).*
Handsaker et al. Discovery and genotyping of genome structural polymorphism by sequencing on a population scale. Nature Genetics, vol. 43, No. 3, pp. 269-276, Feb. 13, 2011, including pp. 1/2-2/2 of Online Methods. (Year: 2011).*
Escaramis et al. PeSV-Fisher: Identification of Somatic and Non-Somatic Structural Variants Using Next Generation Sequencing Data. PLoS One, vol. 8, No. 5, E63377, May 21, 2013, printed as pp. 1-10, pp. 1-5 of Supplementary Information, and Figs. S1 and S2. (Year: 2013).*
Alexej Abyzov et al., "CNVnator: An approach to discover, genotype, and characterize typical and atypical CNVs from family and population genome sequencing," Genome Research, 2011, pp. 974-985, Cold Spring Harbor Laboratory Press.

* cited by examiner

*Primary Examiner* — Jennifer Dunston

(57) ABSTRACT

Disclosed are a method and an apparatus for detecting a translocation. The apparatus acquires BAM for a first pair of chromosomes and a second pair of chromosomes. Also, the apparatus detects a translocation generated in at least one chromosome by selecting at least one translocation case corresponding to the translocation information produced on the basis of BAM from among multiple translocation cases in which a translocation may be generated in at least one of the first and the second chromosomes.

16 Claims, 21 Drawing Sheets

| | | TYPE (A) | TYPE (B) | TYPE (C) | TYPE (D) | TYPE (E) | TYPE (F) | TYPE (G) | TYPE (H) |
|---|---|---|---|---|---|---|---|---|---|
| RD | 1ST PAIR OF CHROMOSOMES | x1.5 | x2.0 | x0.5 | x1.0 | x1.5 | x0.0 | x0.5 | x1.0 |
| | 2ND PAIR OF CHROMOSOMES | x0.5 | x0.0 | x1.5 | x1.0 | x0.5 | x2.0 | x1.5 | x1.0 |
| DF | 5 TO 3 | X | X | O | O | O | O | O | O |
| | 3 TO 5 | O | O | X | O | O | X | O | O |
| CF | 1ST PAIR OF CHROMOSOMES | O | O | O | O | X | X | X | X |
| | 2ND PAIR OF CHROMOSOMES | O | X | O | O | X | O | O | X |

FIG. 7 chr 16    72280000    chr 20    5042000    10    1
>Translocation_3to5_xxx_0000000<

FIG. 8

METHOD AND APPARATUS FOR DETECTING TRANSLOCATION

CROSS REFERENCE TO RELATED APPLICATION(S)

This application claims the benefit of Korean Patent Application No. 10-2014-0165379, filed Nov. 25, 2014, and Korean Patent Application No. 10-2015-0108842, filed Jul. 31, 2015, which are hereby incorporated by reference in its entirety into this application.

BACKGROUND OF THE INVENTION

1. Technical Field

The following embodiments relate to genome analysis. More particularly, the following embodiments disclose a method and an apparatus for detecting chromosomal translocation.

2. Description of the Related Art

DNA, a molecule that carries most of the genetic instructions in organisms including humans, is composed of nucleotides, each having a nucleobase, that is, adenine, cytosine, guanine, or thymine, which are abbreviated by single letter codes A, C, G and T, respectively Genome analysis is a process for analyzing the difference between two DNA sequences. For example, DNA sequences to be compared may be derived from different persons. Thus, genome analysis is also called genome variation analysis.

With the development of next-generation sequencing technology, active research into genome analysis has been conducted.

Of genome variations, structural variation (SV) is the variation in structure of an organism's chromosome, and typically affects a sequence length about 1 kb or greater. Since many structural variants are associated with genetic diseases, structural variations have recently been under intensive study.

Structural variation usually includes deletions, duplications, inversions and translocations. Thus far, extensive research has focused on finding deletions and duplications. In recent years, detection of inversions and translocations has been studied. However, there still exist many false positives in detecting inversions and translocations. The existence of such false positives makes it difficult for biologists to utilize their research results in the field.

For the analysis of structural variations, detection may be carried out taking advantage of information of read depth (RD), paired end (PE), and split read (SR).

RD refers to the number of times a nucleotide sequence is read at each locus of a genome.

Traditionally, a method utilizing RD is widely applied to the analysis of copy number variation (CNV). However, methods utilizing RD are limited in detecting copy number-neutral SVs including inversions and translocations.

Methods using PE and/or SR are effective in detecting the position of an SV break point (BP), irrespective of whether the copy number is neutral or not. With regard to a genome characterized by diploidy, however, methods using PE and/or SR are unable to provide information on whether SV is present either or both of the paired chromosomes.

By integrating information on RD, PE and SR, attempts have been made to overcome the disadvantages arisen when information on RD, PE and SR is separately utilized. Nonetheless, limitations of conventional methods for detecting translocations still remain unsolved due to the complexity of translocations.

With regard to translocations on genomes, reference may be made to Korean Patent Unexamined Application Publication No. 2014-0061223, U.S. Patent Application No. 20130158885, and U.S. Pat. No. 7,948,564.

SUMMARY OF THE INVENTION

An embodiment of the present invention provides a method and apparatus for effectively detecting a translocation by genome analysis.

Another embodiment of present invention provides a method and apparatus for analyzing a translocation, using information about a concordant fragment present in a break point region of structural variation.

Another embodiment of the present invention provides a method and apparatus for determining the presence of a translocation in either or both of paired chromosomes by restoring a ploidy state of a break point.

Another embodiment of the present invention provides a method and apparatus for detecting a translocation that is copy number variable or copy number neutral.

In accordance with an aspect thereof, the present invention provides a method for detecting a translocation, comprising: acquiring a binary version of sequence alignment/map (BAM) for a first chromosome and a second chromosome; and detecting a translocation generated in at least one chromosome by selecting at least one translocation case corresponding to the translocation information produced on the basis of BAM from among multiple translocation cases in which a translocation is possibly generated in at least one of the first chromosome and the second chromosome.

In one exemplary embodiment, when at least one translocation occurs on at least one chromosome, the multiple translocation cases may be expressed by the number of the chromosomes in—the first paired chromosomes on which the translocation occurs, and the number of the chromosomes in the second paired chromosomes on which the translocation occurs.

In another exemplary embodiment, the translocation information may contain discordant fragment (DF) information.

In another exemplary embodiment, the DF information may show at least one BP (break point) present in the first chromosome or the second chromosome.

In another exemplary embodiment, the detecting step may comprise: analyzing at least one BP with the aid of paired end (PE) information and split-read (SR) information of BAM to produce DF information about at least one BP; and utilizing the DF information to select at least one corresponding to at least one BP from among all or a part of the multiple translocation cases.

In another exemplary embodiment, when the DF information indicates presence of '5 to 3' BP on at least one of the first chromosomes and the second chromosome, the at least one selected from among all or a part of the possible multiple translocation cases may include a translocation case in which a translocation is generated on at least one of the first paired chromosomes.

In another exemplary embodiment, when the DF information indicates presence of '3 to 5' BP on at least one of the first chromosomes and the second chromosome, the at least one selected from among all or a part of the multiple translocation cases includes a translocation case in which a translocation is generated on at least one of the paired second chromosomes.

In another exemplary embodiment, the translocation information may contain ploidy information about ploidy in a vicinity of a break point (BP) region on the first chromosome, and ploidy in a vicinity of a BP region on the second chromosome.

In another exemplary embodiment, the detecting step may comprise: analyzing the RD information of BAM to determine ploidy in a vicinity of a BP region on the first chromosome and in a vicinity of a BP region on the second chromosome; and selecting at least one translocation case corresponding to the ploidy in a vicinity of a BP region on the first chromosome and at least one translocation case corresponding to the ploidy in a vicinity of a BP region on the second chromosome from among from all or a part of the possible multiple translocation cases.

In another exemplary embodiment, when a ploidy in a vicinity of a BP region on the first chromosome is smaller than a mean RD, the at least one translocation case selected may account for a translocation case in which a translocation is generated on the first chromosome among all or a part of the possible multiple translocation cases.

In another exemplary embodiment, when a ploidy in a vicinity of a BP region on the second chromosomes is smaller than a mean RD, the at least one translocation case selected may account for a translocation case in which a translocation is generated on the second chromosome among all or a part of the possible multiple translocation cases.

In another exemplary embodiment, the translocation information may contain concordant fragment (CF) information.

In another exemplary embodiment, the CF information may indicate whether or not a CF is in a vicinity of a BP region on the first chromosome and where or not a CF is in a vicinity of a BP region one the second chromosome.

In another exemplary embodiment, the detecting step may comprise: utilizing BAM to produce information about the presence of CF in a vicinity of at least one BP present on the first chromosome or the second chromosome; and selecting at least one translocation case corresponding to the information about CF presence from among from all or a part of the multiple translocation cases.

In another exemplary embodiment, the translocation information may contain at least a part of DF information about, ploidy in a vicinity of a BP region on the first chromosome, polidy in a vicinity of a BP region on the second chromosome, and information about CF presence.

In another exemplary embodiment, the DF information may show at least one BP present in the first chromosome or the second chromosome.

In another exemplary embodiment, when the DF information indicates the absence of '5 to 3' BP and the presence of '3 to 5' BP while the CF information means the presence of a CF in each of the first and the second chromosomes, the at least one translocation case selected may be a translocation case in which a translocation exists in one of the second paired chromosomes, but not in any of the first paired chromosomes.

In another exemplary embodiment, when it is determined that the ploidy in a vicinity of a BP region on the first chromosome is two times the mean RD and the ploidy in a vicinity of a BP region on the second chromosome is zero, the at least one translocation case selected may be a translocation case in which a translocation exists in both of the second paired chromosomes, but not in any of the first paired chromosomes.

In another exemplary embodiment, when the DF information indicates the presence of '5 to 3' BP and the absence of '3 to 5' BP while the CF information teaches the presence of CF in each of the first and the second chromosomes, the at least one translocation case selected may be a translocation case in which a translocation is present in one of the first paired chromosomes and absent in both of the second paired chromosomes.

In another exemplary embodiment, when the DF information produced explains the presence of both '5 to 3' BP and '3 to 5' BP while the CF information indicates the presence of CF in each of the first and the second chromosome, the at least one translocation case selected may be a translocation case in which a translocation is present in one of the first paired chromosomes and in one of the second paired chromosomes.

In another exemplary embodiment, when the DF information explains the presence of both '5 to 3' BP and '3 to 5' BP while the CF information indicates the presence of CF in the first chromosome and the absence of CF in the second chromosome, the at least one translocation case selected may be a translocation case of in which a translocation is present in one of the first paired chromosomes and in both of the second paired chromosomes.

In another exemplary embodiment, when it is determined that the ploidy in a vicinity of a BP region on the first chromosomes is zero and the ploidy in a vicinity of a BP region on the second chromosomes is two times the mean RD, the at least one translocation case selected may be a translocation case of in which a translocation exists in both of the first paired chromosomes, but not in any of the second paired chromosomes.

In another exemplary embodiment, when the DF information explains the presence of both '5 to 3' BP and '3 to 5' BP while the CF information indicates the absence of CF in each of the first chromosome and the presence of CF in the second chromosome, the at least one translocation case selected may be a translocation case in which a translocation is present in both of the first paired chromosomes and in one of the second paired chromosomes.

In another exemplary embodiment, when the DF information explains the presence of both '5 to 3' BP and '3 to 5' BP while the CF information indicates the absence of CF in both the first and the second chromosomes, the at least one translocation case selected may be a translocation case in which a translocation is present in both of the first paired chromosomes and in both of the second paired chromosomes.

In accordance with another aspect thereof, the present invention provides an apparatus for detecting a translocation, comprising: an acquirement unit for acquiring binary version of sequence alignment/map (BAM) for a first chromosome and a second chromosome; and a detection unit for detecting a translocation generated in at least one chromosome by selecting at least one translocation case corresponding to the translocation information produced on the basis of BAM from among multiple translocation cases in which a translocation may be generated in at least one of the first and the second chromosomes.

In addition, embodiments of the present invention further provide other methods, apparatuses and systems for implementing the present invention, and computer readable media or computer program products for performing various computer-implemented operations.

BRIEF DESCRIPTION OF THE DRAWINGS

The above and other objects, features and advantages of the present invention will be more clearly understood from the following detailed description taken in conjunction with the accompanying drawings, in which:

FIG. 7 is a table in which RD, DF and CF patterns for translocations are analyzed in accordance with an embodiment of the present invention;

FIG. 8 shows results of a BP analysis test in accordance with an embodiment of the present invention;

DESCRIPTION OF THE PREFERRED EMBODIMENTS

Figure 1:
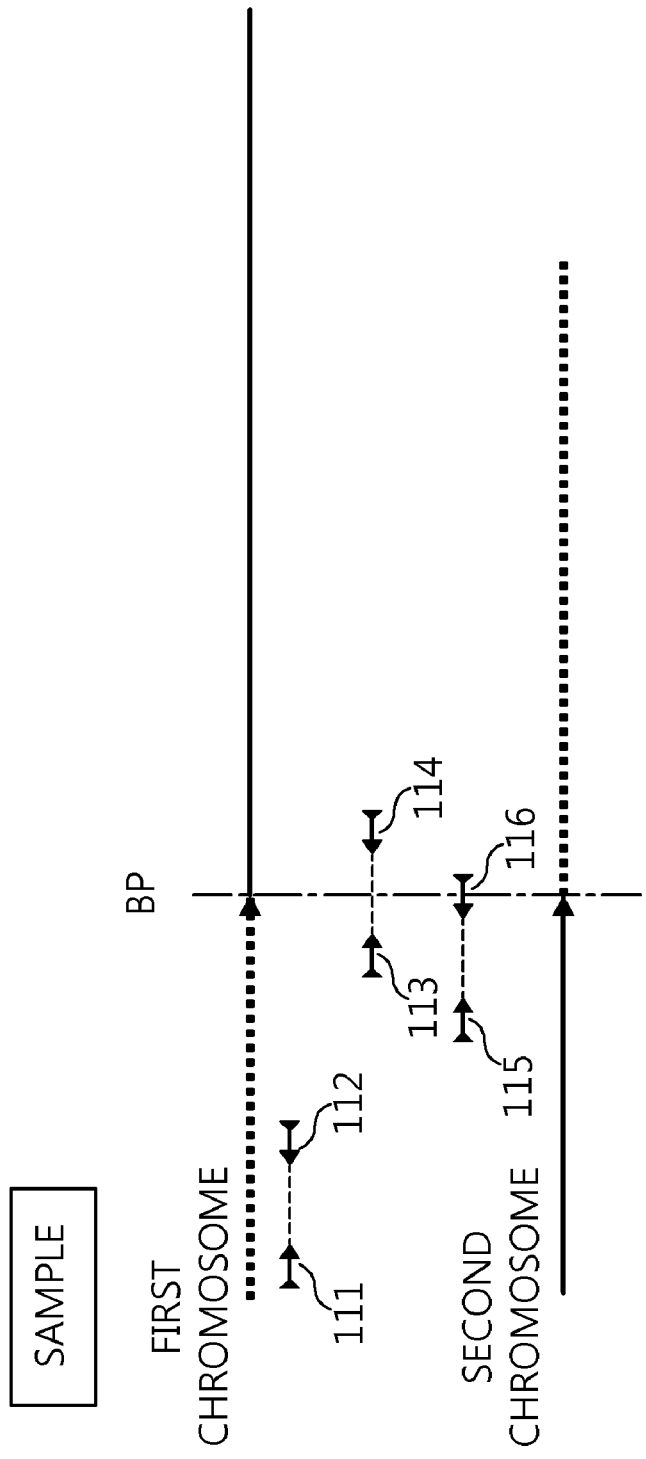
FIG. 1 is a schematic view of a sample acquired by next-generation sequencing in accordance with an exemplary embodiment of the present invention.

Before the present systems and methods are described, it is to be understood that this invention is not limited to particular data, software, hardware or method steps described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The present invention will be described in detail below with reference to the accompanying drawings. Repeated descriptions and descriptions of known functions and configurations which have been deemed to make the gist of the present invention unnecessarily obscure will be omitted below. The embodiments of the present invention are intended to fully describe the present invention to a person having ordinary knowledge in the art to which the present invention pertains. Accordingly, the shapes, sizes, etc. of components in the drawings may be exaggerated to make the description clearer.

Herein, the terms 'genome' and 'gene' may be used interchangeably.

FIG. 1 is a schematic view of a sample acquired by next-generation sequencing in accordance with an exemplary embodiment of the present invention, In FIG. 1, the upper horizontal line may represent a first gene while the lower horizontal line may account for a second gene.

On the first gene, the solid line may represent a region where a translocation occurs. A point at which a dotted line is changed into a solid line on the first gene may be represented by a BP.

On the second gene, the dotted line may represent a region where a translocation occurs. A point at which a solid line is changed into a dotted line on the second gene may be represented by a BP.

NGS may be a technique in which entire genes of a sample are amplified and the amplified genes are cut into very short fragments, followed by reading the fragments. For instance, the fragments may range in length from 35 to 150 bases.

By NGS, as shown in FIG. 1, fragments including a first fragment 111, a second fragment 112, a third fragment 113, a fourth fragment 114, a fifth fragment 115 and a sixth fragment 116 may be obtained. In other words, a first fragment 111, a second fragment 112, a third fragment 113, a fourth fragment 114, a fifth fragment 115 and a sixth fragment 116 may be NGS data of the sample.

The fragments may pair, like the first fragment 111 and the second fragment 112. A read fragment may refer to a pair of fragments, such as the first fragment 111 and the second fragment 112. Further, a pair of the third fragment 113 and the fourth fragment 114 is a read fragment. Likewise, the fifth fragment 115 and the sixth fragment 116 may pair to form a read fragment.

Read sequences may mean individual sequences of read fragments.

Figure 2:
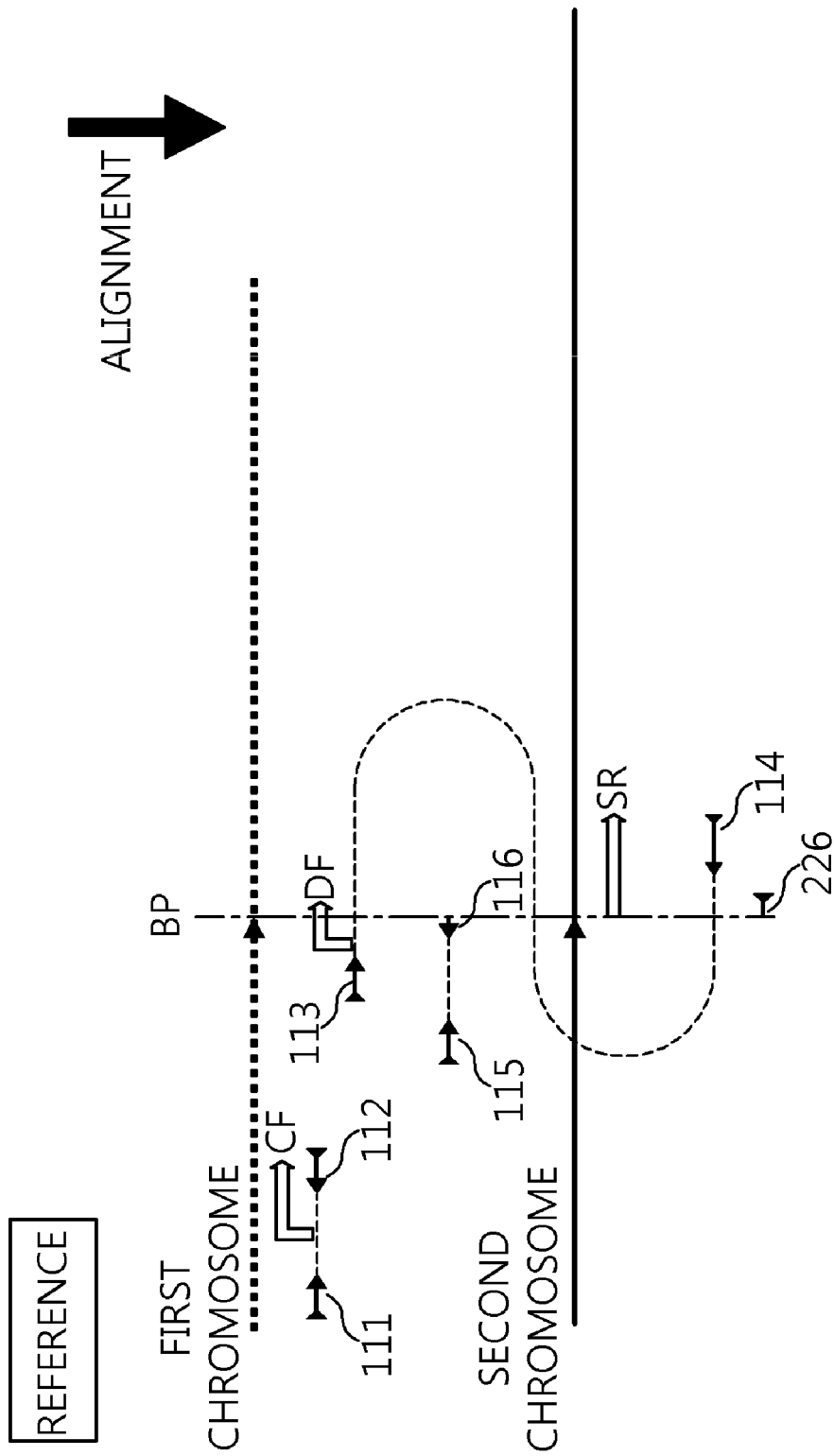
FIG. 2 elucidates translocations generated in a sample by comparison with a reference according to one exemplary embodiment.

With reference to FIG. 2, translocations generated in a sample are elucidated by comparison with a reference according to one exemplary embodiment.

FIG. 2 may show read alignments of read sequences.

Returning to FIG. 1, a solid line portion on the first gene may be translocated from a portion of the second gene in view of the reference sequence. In addition, a solid line portion on the second gene may be translocated from a portion of the first gene in view of the reference sequence.

As used herein, the term "read alignment" refers to a process of identifying respective positions on a reference sequence corresponding to the NGS data of a sample including the first fragment 111, the second fragment 112, the third fragment 113, the fourth fragment 114, the fifth fragment 115, and the sixth fragment 116.

A read alignment process may determine positions of the read sequences acquired from the sample on the reference sequence.

After read alignment, read fragments and/or read sequences may be classified as follows, according to the characteristics relevant to alignment:

1) Concordant Fragment (CF): when the full length of a read fragment is positioned within an allowable range, the read fragment may be a CF. In FIG. 1, for example, the first fragment 111 and the second fragment 112 form a pair as a read fragment, and the full length of the read fragment corresponding to a pair of the first fragment 111 and the second fragment 112 are within the allowable range. Accordingly, the read fragment of the first fragment 111 and the second fragment 112 may be a CF.

2) Discordant Fragment (DF): when the full length of a read fragment is not completely within an allowable range, the read fragment may be a DF. In FIG. 1, for instance, a third fragment 113 and a fourth fragment 114 form a pair as a read fragment, and the full length of the read fragment corresponding to a pair of the third fragment 113 and the fourth fragment 114 deviates from the allowable range. Therefore, a read fragment for the third fragment 113 and the fourth fragment 114 may be a DF.

3) Split Read (SR): when one read sequence is aligned in the form of two split genes, the read fragment may be SR. When a part of the read sequence is aligned within one gene while the other is aligned within another gene, the read fragment may be SR. In FIG. 1, for example, one a part of a sixth fragment 116 is aligned within the first gene while the other is aligned within another gene. Hence, a read fragment for the fifth fragment 115 and the sixth fragment 116 may be SR. In FIG. 2, the sixth fragment 116 is split into two fragments 216 and 226.

FIGS. 3a to 3i explain original chromosomes and corresponding multiple translocation cases that are likely to occur in accordance with an exemplary embodiment of the present invention.

For detecting a translocation, a pattern analysis of NGS data obtained in a translocation region is required.

Figure 3A:
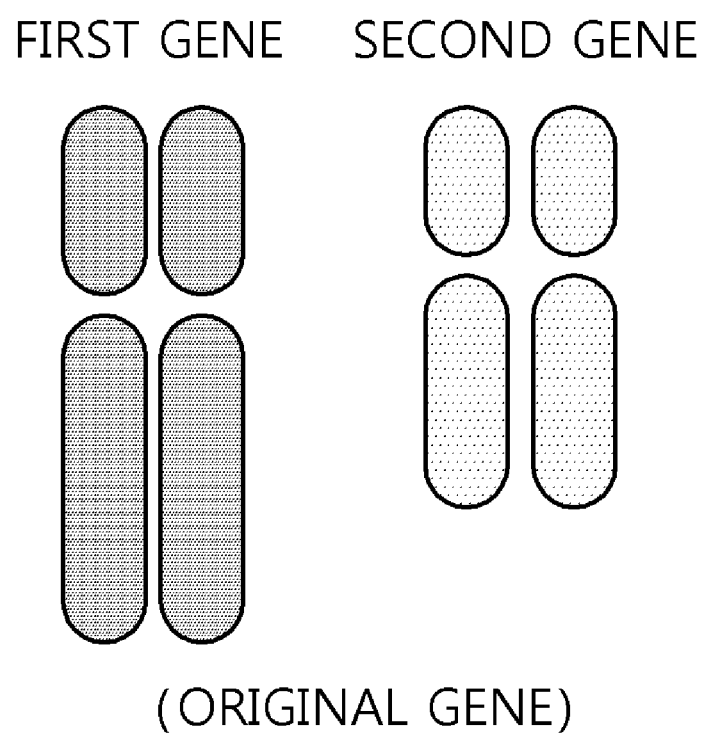
FIG. 3a represents original chromosomes in accordance with an embodiment of the present invention.

In FIG. 3a, original chromosomes are depicted. FIGS. 3b to 3i show respective translocation cases in which at least one chromosome undergoes translocation.

In FIGS. 3b to 3i, there are the translocation cases that account for possible combinations of translocations. These translocation cases may include cases in which a translation, after being generated, may run in the progeny.

In FIGS. 3a to 3i, first chromosomes are a pair of chromosomes, and second chromosomes also form a pair of chromosomes.

As shown in FIGS. 3a to 3i, the first pair chromosomes and the second pair chromosomes are positioned as a left panel and a right panel, respectively. Further, the first chromosomes are depicted to be relatively long, compared to the second chromosomes.

In FIG. 3a, the first chromosomes appear dark while the second chromosomes are lightly shaded.

Hence, a lightly shaded portion on the first chromosomes may explain a translocation generated on the first chromosome in FIGS. 3b to 3i. Of the second chromosomes, a darkly shaded portion may represent a translocation generated on the second chromosomes.

FIG. 3a represents original chromosomes in accordance with an embodiment of the present invention.

As used herein, the term "original chromosome" means a chromosome in which no translocations have been generated.

Figure 3B:
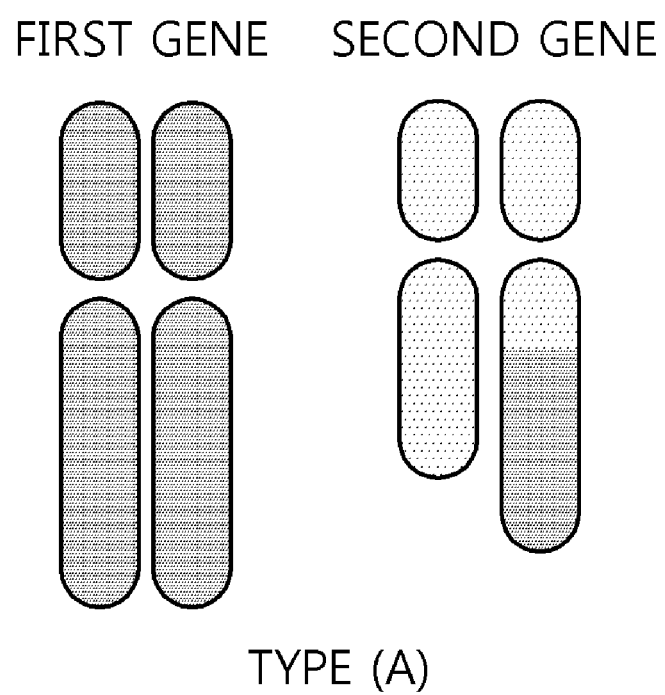
FIG. 3b shows a translocation case of type (a) in accordance with an exemplary embodiment of the present invention.

FIG. 3b shows a translocation case of type (a) in accordance with an exemplary embodiment of the present invention.

In the translocation case of type (a), no translocations are present in the first paired chromosomes while one of the second paired chromosomes underwent translocation.

Figure 3C:
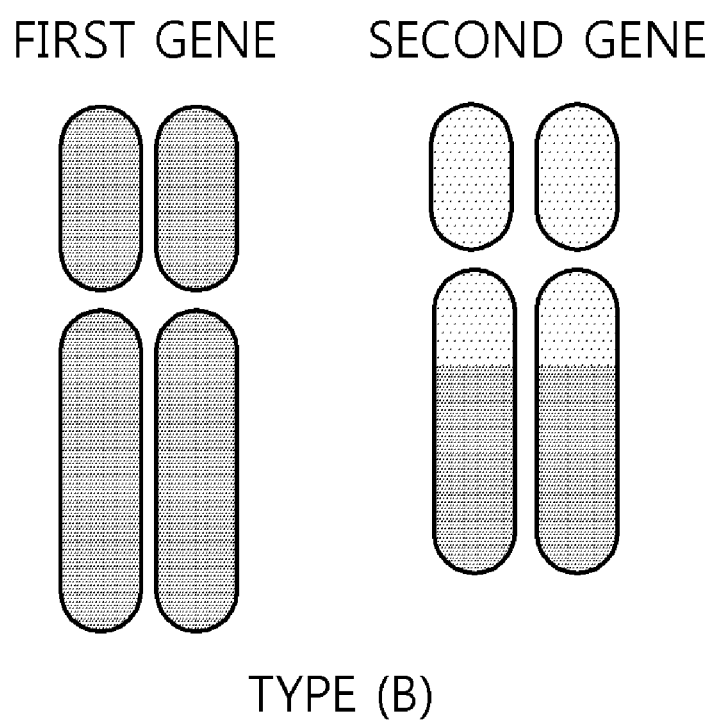
FIG. 3c shows a translocation case of type (b) in accordance with another exemplary embodiment of the present invention.

FIG. 3c shows a translocation case of type (b) in accordance with another exemplary embodiment of the present invention.

In the translocation case of type (b), no translocations are present in the first paired chromosomes while both of the second paired chromosomes have a translocation.

Figure 3D:
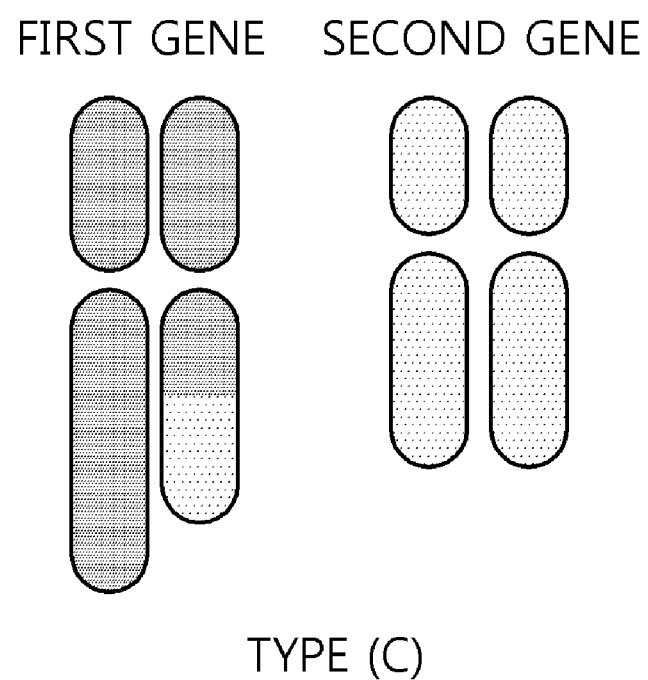
FIG. 3d shows a translocation case of type (c) in accordance with another exemplary embodiment of the present invention.

FIG. 3d shows a translocation case of type (c) in accordance with another exemplary embodiment of the present invention.

In the translocation case of type (c), one of the first paired chromosomes has a translocation while no translocations are present in the second paired chromosomes.

Figure 3E:
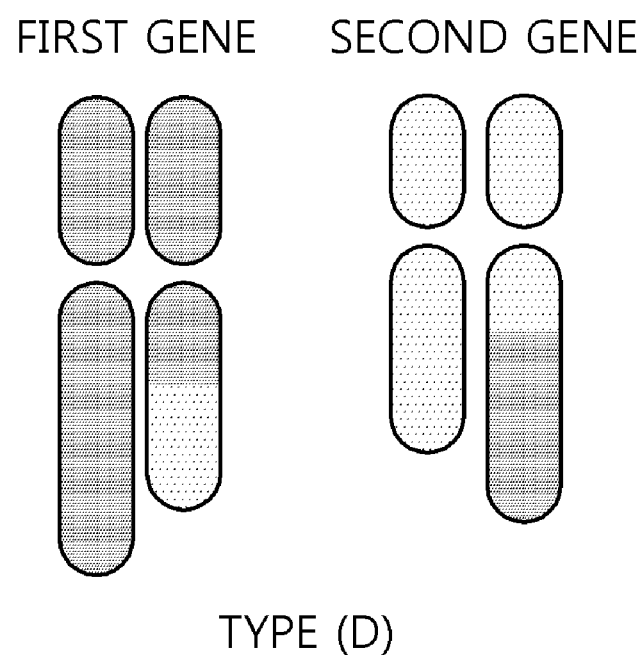
FIG. 3e shows a translocation case of type (c) in accordance with another exemplary embodiment of the present invention.

FIG. 3e shows a translocation case of type (c) in accordance with another exemplary embodiment of the present invention.

In the translocation case of type (d), one of the first paired chromosomes has a translocation and one of the second paired chromosomes has a translocation.

Figure 3F:
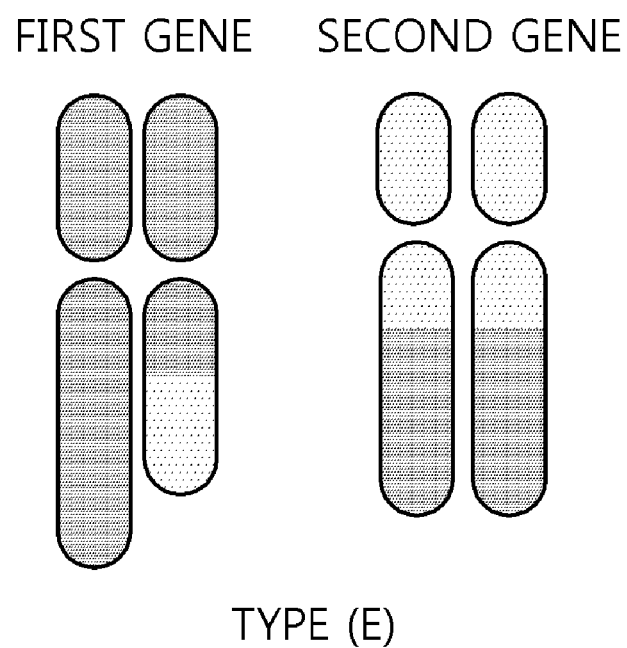
FIG. 3f shows a translocation case of type (e) in accordance with another exemplary embodiment of the present invention.

FIG. 3f shows a translocation case of type (e) in accordance with another exemplary embodiment of the present invention.

In the translocation case of type (e), one of the first paired chromosomes has a translocation and both of the second paired chromosomes have a translocation.

Figure 3G:
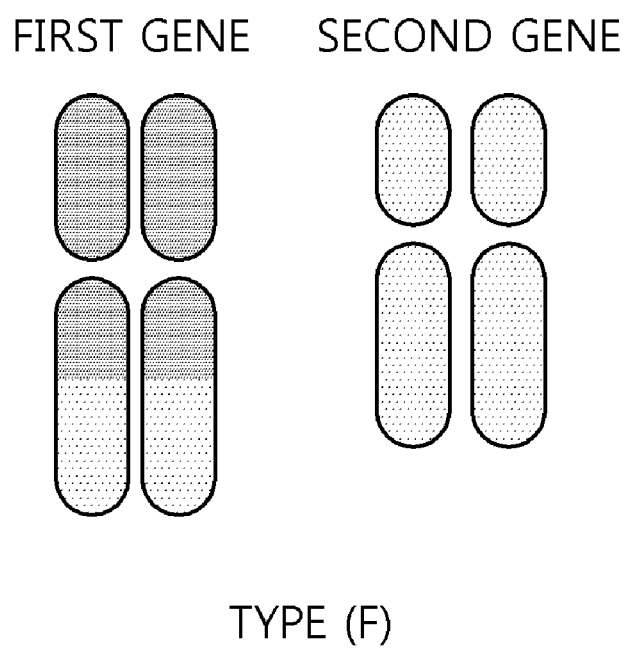
FIG. 3g shows a translocation case of type (f) in accordance with another exemplary embodiment of the present invention.

FIG. 3g shows a translocation case of type (f) in accordance with another exemplary embodiment of the present invention.

In the translocation case of type (f), both of the first paired chromosomes have a translocation while none of the second paired chromosomes have a translocation.

Figure 3H:
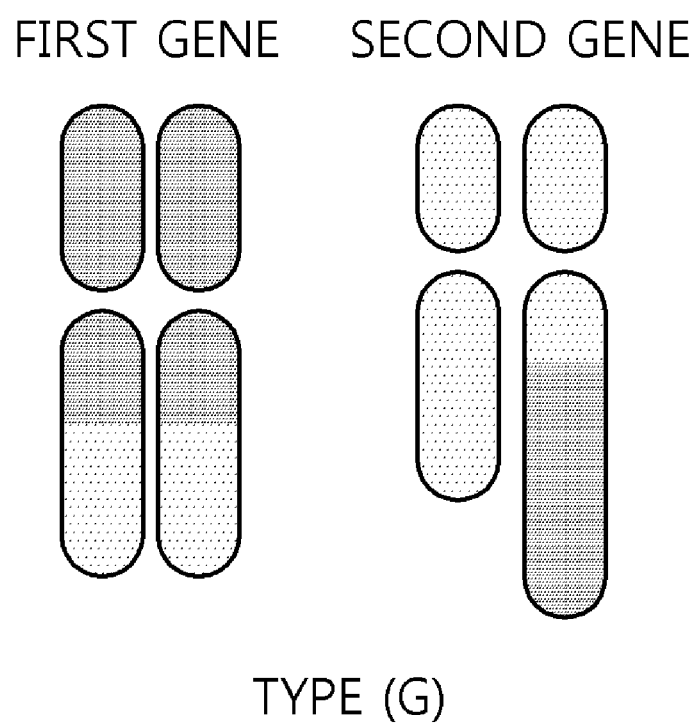
FIG. 3h shows a translocation case of type (g) in accordance with another exemplary embodiment of the present invention.

FIG. 3h shows a translocation case of type (g) in accordance with another exemplary embodiment of the present invention.

In the translocation case of type (g), both of the first paired chromosomes have a translocation while one of the second paired chromosomes has a translocation.

Figure 3I:
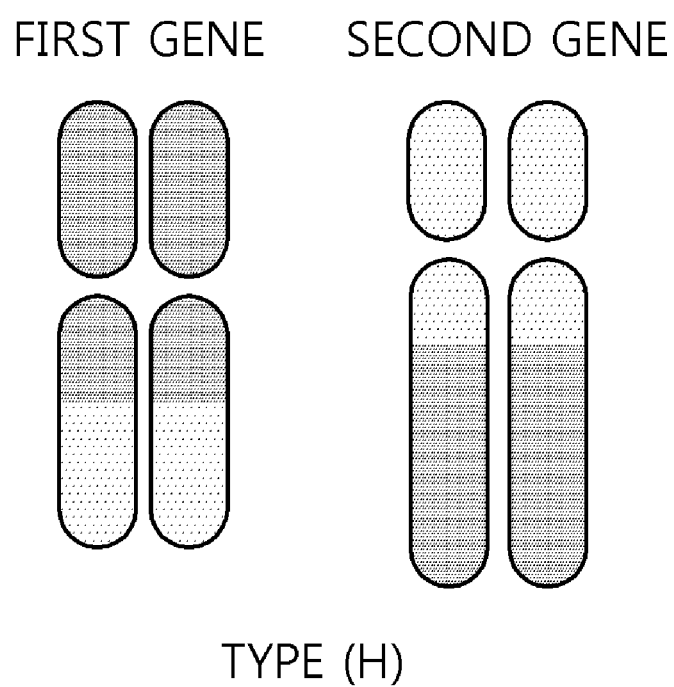
FIG. 3i shows a translocation case of type (h) in accordance with another exemplary embodiment of the present invention.

FIG. 3i shows a translocation case of type (h) in accordance with another exemplary embodiment of the present invention.

In the translocation case of type (h), both of the first paired chromosomes have a translocation and both of the second paired chromosomes has a translocation.

Figure 4:
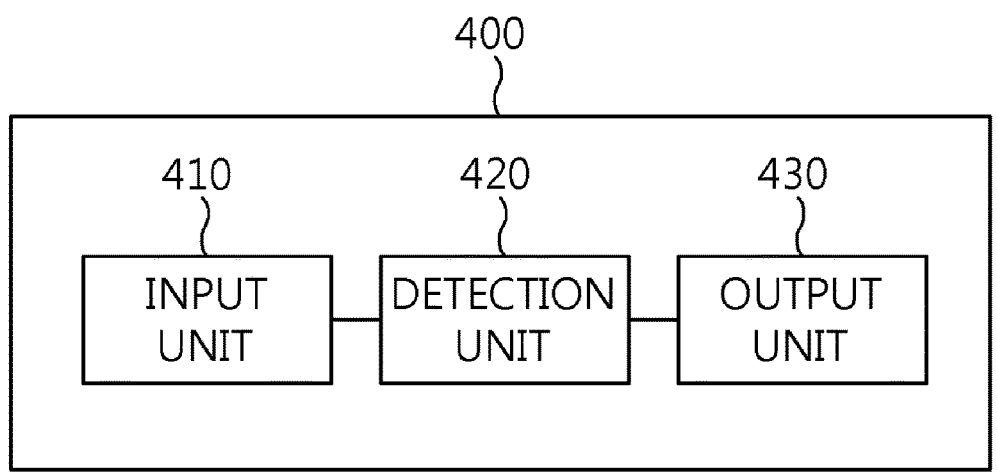
FIG. 4 is a schematic structural view of an apparatus for detecting a translocation in accordance with an exemplary embodiment of the present invention.

FIG. 4 is a schematic structural view of an apparatus for detecting a translocation in accordance with an exemplary embodiment of the present invention.

As can be seen, a translocation-detecting apparatus 400 in accordance with an embodiment of the present invention may comprise an input unit 410, a detection unit 420, and an output unit 430.

The input unit 410 may acquire binary version of sequence alignment/map (BAM) for the first and the second chromosomes.

BAM may include data about the alignments of multiple read sequences obtained by NGS with a reference sequence.

BAM may be a computer system file. BAM may be an input file of the translocation detecting apparatus.

The detection unit 420 may detect a translocation generated in at least one chromosome by selecting at least one corresponding to the translocation information produced on the basis of BAM from among multiple translocation cases in which a translocation may be generated in at least one of the first and the second chromosomes.

The output unit 430 may output information on the detected translocation.

A detailed description will be given of functions and operations of the input unit 410, the detection unit 420, and the output unit 430.

As shown in FIG. 4, a translocation detecting apparatus 400 according to an embodiment of the present invention may comprise an input unit 410, a detection unit 420, and an output unit 430. In one exemplary embodiment, at least a part of each of the input unit 410, the detection unit 420, and the output unit 430 may be a program module that can communicate with an external device or system. These program modules may be included in the form of operating systems, applied program modules, or other program modules in the translocation detecting apparatus 400, and may be physically stored in various memory devices. In addition, at least a part of the program modules may be stored in a remote memory device that can communicate with the translocation detecting apparatus 400. Examples of the program modules may include, but are not limited to, a routine, a subroutine, a program, an object, a component, and a data structure, which perform specific functions or operations, as will be described later, in accordance with the present invention. The program modules may be composed of instructions or codes that are executed by at least one processor of the translocation detecting apparatus 400.

Figure 5:
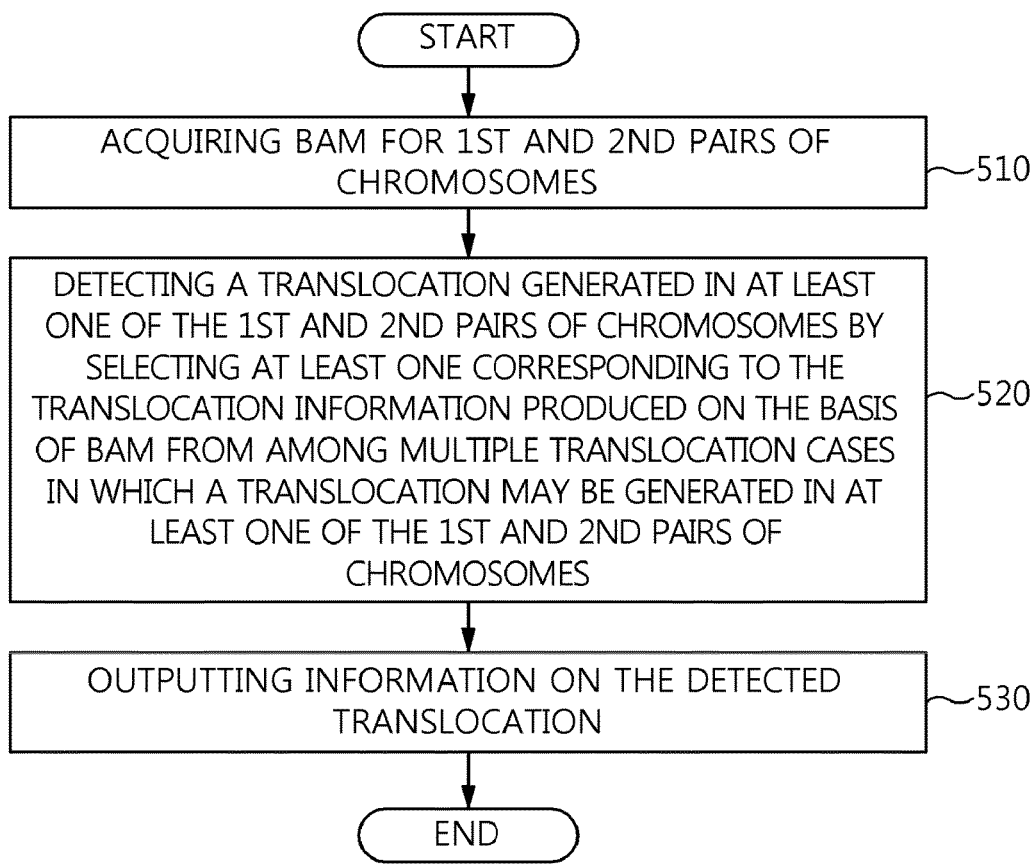
FIG. 5 is a flow chart illustrating a method for detecting a translocation in accordance with an embodiment of the present invention.

FIG. 5 is a flow chart illustrating a method for detecting a translocation in accordance with an embodiment of the present invention.

In step (510), the input unit 410 may acquire BAM for the first chromosomes and the second chromosomes.

In step (520), the detection unit 420 may detect a translocation generated in at least one of the chromosomes by selecting at least one corresponding to the translocation information produced on the basis of BAM from among multiple translocation cases in which a translocation may be generated in at least one of the first and the second chromosomes.

In step 530, output unit 430 may output information on the detected translocation. The information on the detected translocation may be information about at least one selected from among multiple translocation cases in which a translocation may be generated on at least one of the first chromosomes and the second chromosomes.

Hereinafter, the phrase "multiple translocation cases in which a translocation may be generated on at least one of the first chromosomes and the second chromosomes" will be abbreviated to "possible multiple translocation cases".

The translocation information may contain at least one of discordant fragment (DF) information about at least one chromosome, ploidy information about at least one chromosome, and concordant fragment (CF) information about at least one chromosome. The ploidy information may include ploidy in a vicinity of a break point (BP) region on the first chromosomes, and ploidy in a vicinity of a BP region on the second chromosomes.

The DF information may show at least one BP present in the first chromosomes or the second chromosomes.

The CF information may indicate whether or not a CF is in a vicinity of a BP region on the first chromosomes and where or not a CF is in a vicinity of a BP region one the second chromosomes.

When a translocation occurs on at least one chromosome, the possible multiple translocation cases may be expressed by the number of the chromosomes in the first paired chromosomes on which the translocation occurs, and the number of the chromosomes in the second paired chromosomes on which the translocation occurs. In translocation cases, the number of the chromosomes in the first paired chromosomes on which a translocation occurs may be 0, 1 or 2. Likewise, the number of the chromosomes in the second paired chromosomes on which a translocation occurs may be 0, 1 or 2.

The multiple translocation cases in which a translocation may be generated on at least one of the first chromosomes and the second chromosomes may include all the translocation cases of types (a) to (h) in FIGS. 3b to 3i.

Figure 6:
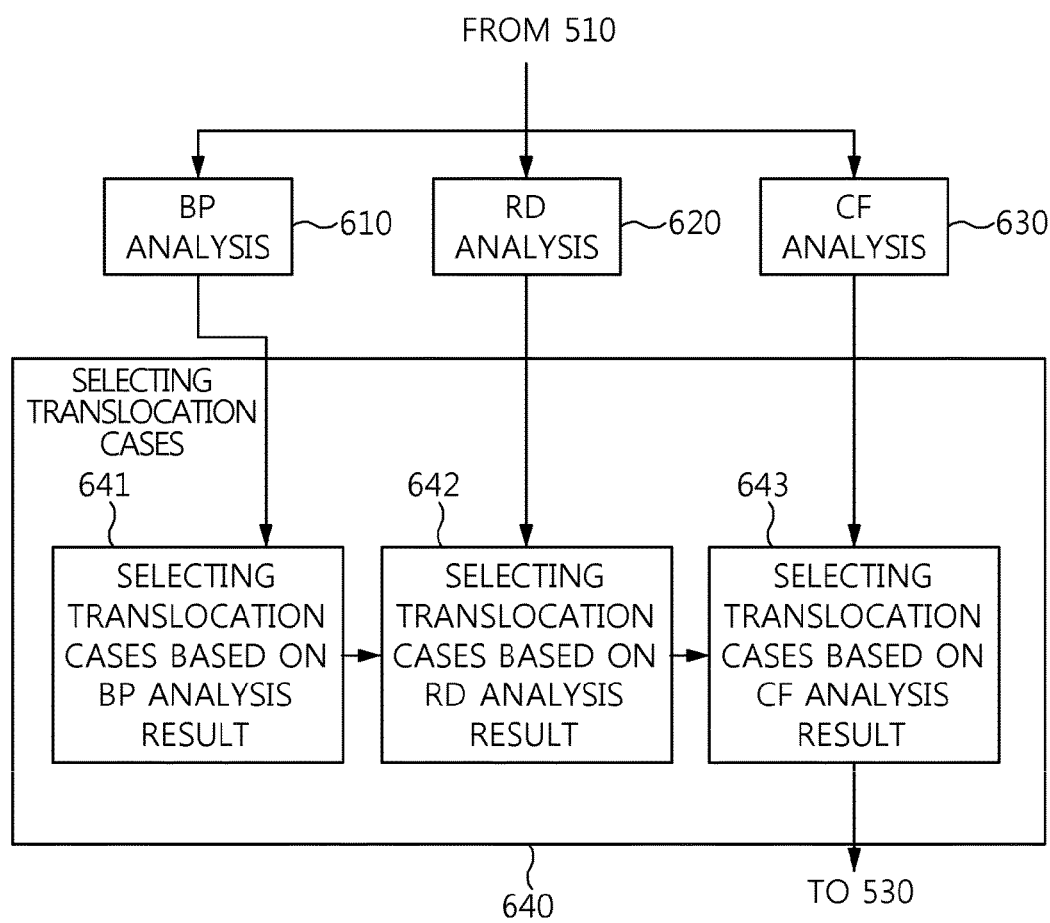
FIG. 6 is a flow chart illustrating a method for detecting a translocation corresponding to translocation information in accordance with an exemplary embodiment of the present invention.

In conjunction with FIG. 6, the above-described translocation information and the method for detecting a translocation that occurs on at least one chromosome will be in detail described.

FIG. 6 is a flow chart illustrating a method for detecting a translocation corresponding to translocation information in accordance with an exemplary embodiment of the present invention.

The step (520) of FIG. 5 may include sub-steps (610), (620), (630), and (640).

In step (610), the detection unit 420 may conduct BP analysis.

In this context, the detection unit 420 may analyze at least one BP with the aid of the paired end (PE) information and split-read (SR) information of BAM to produce DF information about at least one BP. Substantially, PE information may be DF information.

The DF information may include information about whether DF is present on the first chromosomes and whether DF is present on the second chromosomes.

In step (620), the detection unit 430 may conduct RD analysis.

For this, the detection unit 430 may analyze the RD information of BAM to determine ploidy in a vicinity of a BP region on the first chromosomes and in a vicinity of a BP region on the second chromosomes.

Information about the ploidy in a vicinity of a BP region on the first chromosomes may indicate the number of multiplicity of the RD in a vicinity of at a BP region on the first chromosomes relative to mean RD. Likewise, information about the ploidy in a vicinity of a BP region on the second chromosomes may indicate the number of multiplicity of the RD in a vicinity of at a BP region on the second chromosomes relative to mean RD.

In step (630), the detection unit 420 may perform CF analysis.

In this regard, the detection unit 420 takes advantage of BAM to produce information about the presence of CF in a vicinity of at least one BP present on the first or the second chromosomes.

This CF information may include information about the presence of CF in the first chromosomes and in the second chromosomes.

In step (640), the detection unit 420 may use at least one of results of BP, RD, and CF analyses to select at least one from among the multiple translocation cases.

Step (640) may include at least one of steps (641), (642) and (643).

In step (641), the detection unit 420 may use the result of BP analysis to select at least one from among all or a part of possible multiple translocation cases.

The detection unit 420 may perform filtering all or a part of the possible multiple translocation cases, using the result of BP analysis, and may select at least one translocation case coincident with the result of BP analysis from the possible multiple translocation cases through the filtering.

Also, the detection unit 420 may select at least one translocation case corresponding to at least one BP from among from all or a part of the possible multiple translocation cases, using the DF information. Herein, the part of the possible multiple translocation cases may be at least one translocation case selected using either or both of the results of RD analysis and CF analysis.

In step 642, the detection unit 420 may select at least one from among the possible multiple translocation cases, using the result of RD analysis.

The detection unit 420 may perform filtering of all or a part of the possible multiple translocation cases, using the result of RD analysis, and may select at least one translocation case coincident with the result of RD analysis from the possible multiple translocation cases through the filtering.

Also, the detection unit 420 may select at least one translocation case corresponding to the ploidy in a vicinity of a BP region on the first chromosomes and at least one translocation case corresponding to the ploidy in a vicinity of a BP region on the second chromosomes from among from all or a part of the possible multiple translocation cases. Herein, the part of the possible multiple translocation cases may be at least one translocation case selected using either or both of the results of BF analysis and CF analysis.

In step 643, the detection unit 420 may select at least one from among the possible multiple translocation cases, using the result of CF analysis.

The detection unit 420 may perform filtering of all or a part of the possible multiple translocation cases, using the result of CF analysis, and may select at least one translocation case coincident with the result of CF analysis from the possible multiple translocation cases through the filtering.

Also, the detection unit 420 may select at least one translocation case corresponding to the CF existence information from among from all or a part of the possible multiple translocation cases.

The steps (610), (620), (630), (640), (641), (642) and (643) may be conducted in an order different from that shown in FIG. 6. For example, step (610), step (641), step (620), step (642), step (630) and step (643) may be carried out in that order. The order of carrying out step (610), step (620) and step (630) may be interchanged, and step (641), step (642), and step (643) can be conducted in an order corresponding to the order change. For instance, no limitations may be imposed on the order of conducting the steps (610), (620), (630), (640), (641), (642) and (643), with the exception that steps (610), (620) and (630) are conducted ahead of steps (641), (642) and (643), respectively.

In addition, a part of the steps (610), (620), (630), (641), (642), and (643) of FIG. 6 may be omitted. When a translocation case or no translocation cases are selected by conducting a part of the steps (610), (620), (630), (641), (642), and (643), the other steps may be not carried out. For example, when the selection of a certain translocation case is determined by conducting steps (610) and (641), the other steps (620), (630), (642) and (643) may be not carried out.

FIG. 7 is a table in which RD, DF and CF patterns for translocations are analyzed in accordance with an embodiment of the present invention In FIG. 7, the translocation cases of types (a) to (h) in the first line are possible combinations of translocation cases shown in FIGS. 3b to 3i.

In the lines of RD of FIG. 7, RD for the types of the translocation cases are numerically expressed. In this regard, the numbers for RD may be values for translocation regions.

Each column of the lines of RD expresses RD for the translocation case type indicated by the top column. Of the lines of RD, the upper line and the lower line express RD of the first chromosomes and the second chromosomes, respectively. The lines of RD may contain information on ploidy in a vicinity of BP regions on the first chromosomes and the second chromosomes, described in conjunction with FIG. 6.

Depending on the multiplicity of amplification of NGS data, RD may vary. For instance, when NGS data is amplified 30-fold, the theoretical mean RD may be 30.

In FIG. 7, a value of mean RD is set to be 'x1.0'. Hence, the RD increased or decreased on the basis of the mean RD is expressed as 'x0.0', 'x0.5', 'x1.5' or 'x2.0'. The RD of 'x1.0' may be the same as the mean RD. The expressions 'x0.0', 'x0.5', 'x1.5', and 'x2.0' may mean a RD value of 0, 0.5 times, 1.5 times, and 2 times the mean RD, respectively.

In the translocation case of type (a), for example, the RD of the first chromosomes may be 1.5 times the mean RD while the RD of the second chromosomes may be 0.5 times the mean RD. The numbers of multiplicity given in FIG. 7 may be applied to the translocation cases of the other types, and the same descriptions are omitted.

By way of example, a translocation case in which ploidies of the first chromosomes and the second chromosomes are respectively 'x1.5' and 'x0.5' may be the translocation case of type (a) or (e). A translocation case in which the first chromosomes have a ploidy of 'x2.0' and the second chromosomes have a ploidy of 'x0.0' may be the translocation case of type (b). When ploidies of the first chromosomes and the second chromosomes are respectively 'x0.5' and 'x1.5', the translocation case may be of type (c) or type (g). When ploidies of the first chromosomes and the second chromosomes are respectively 'x1.0' and 'x1.0', the translocation case may be of type (d) or type (h). A translocation case in which the first chromosomes and the second chromosomes respectively have ploidies of 'x0.0' and 'x2.0' may be the translocation case of type (f).

In step (620) described in conjunction with FIG. 6, for example, the detection unit 420 may determine the ploidies of the first chromosomes and the second chromosomes to be '×1.5' (that is, 1.5 times the mean RD) and '×0.5' (that is, 0.5 times the mean RD), respectively. For this, the detection unit 420 in step (642) may select the translocation case of type (a) or (e) as at least one translation case corresponding to the ploidies in a vicinity of BP regions on the first chromosomes and the second chromosomes from among all or a part of the possible multiple translocation cases. Similar determination and selection may be applied to other ploidies of the first chromosomes and the second chromosomes. The same descriptions are omitted of the determination and selection.

For instance, when a ploidy in a vicinity of a BP region on the first chromosomes is smaller than the mean RD, at least one translocation case selected in step (642) described in conjunction with FIG. 6 may account for a translocation case in which a translocation is generated on the first chromosomes among all or a part of the possible multiple translocation cases.

When a ploidy in a vicinity of a BP region on the second chromosomes is smaller than the mean RD, at least one translocation case selected in step (642) described in conjunction with FIG. 6 may account for a translocation case in which a translocation is generated on the second chromosomes among all or a part of the possible multiple translocation cases.

In the lines of DF of FIG. 7, DF for the types of the translocation cases are expressed. In this regard, the contents of the DF columns may be of translocations in a vicinity of BP regions.

Each column of the lines of DF expresses DF for the translocation case type indicated by the top column.

A gene is composed of one or two DNA or RNA strands, and the strands have directionality, as expressed with the opposite ends thereof. The strand starts from one end expressed as 5-prime (5') and ends at the other end expressed as 3-prime (3'). The expressions '5 to 3' and '3 to 5' in the lines of DF denote the directionality. '5 to 3' means that BP is detected using a read fragment in the direction from '5-prime read fragment sequence' to '3-prime read sequence '. '3 to 5' means that BP is detected using a read fragment in direction from '3-prime read sequence ' to '5-prime read sequence'.

The lines of DF contain the DF information explained in conjunction with FIG. 6.

In the '5 to 3' line of DF, the presence or absence of DF in the first chromosome is denoted. The mark 'O' indicates the presence of DF in the first chromosomes whereas the mark 'X' denotes the absence of DF in the first chromosomes. In the '3 to 5' line of DF, the presence or absence of DF in the second chromosome is denoted. The mark 'O' indicates the presence of DF in the second chromosomes whereas the mark 'X' denotes the absence of DF in the second chromosomes.

Because DF is absent in the first chromosomes of the translocation case of type (a), the column of type (a) in the '5 to 3' line is marked with 'X'. On the other hand, the mark 'O' of the column of type (a) in the '3 to 5' line accounts for the presence of DF in the second chromosomes of the translocation case of type (a). Such marks may be given to translocations cases of other types, and the same descriptions are omitted.

For example, a translocation case in which DF is absent in the first chromosome but present in the second chromosome may include the translocation case of type (a) and the translocation case of type (b). Within the range of the translocation case in which DF is present in the first chromosomes, but absent in the second chromosome, the trans- location cases of type (c) and type (f) fall. The presence of DF in both the first and the second chromosomes accounts for the translocation cases of types (d), (e), (g), and (h).

In step (610), as described in FIG. 6, the detection unit 420 may produce DF information indicating that DF is absent in the first chromosomes but present in the second chromosomes. For this, the detection unit 420 in step (641) may select a translocation case in which 'X' is given to the '5to 3' line while 'O' is marked on the '3 to 5' line from among all or a part of the possible multiple translocation cases. That is to say, the detection unit 420 in step (641) may select the translocation case of type (a) or type (b) as at least one translocation case corresponding to the DF information from among all or a part of the possible multiple translocation cases. Similar determination and selection may be applied to other DF information. The same descriptions are omitted of the determination and selection.

When DF information indicates the presence of '5 to 3' BP on at least one of the first and the second chromosomes, at least one selected from among all or a part of the possible multiple translocation cases by the step (641) described in conjunction with FIG. 6 includes a translocation case in which a translocation is generated on at least one of the first paired chromosomes.

When DF information indicates the presence of '3 to 5' BP on at least one of the first and the second chromosomes, at least one selected from among all or a part of the possible multiple translocation cases by the step (641) described in conjunction with FIG. 6 includes a translocation case in which a translocation is generated on at least one of the second paired chromosomes.

In the lines of DF of FIG. 7, DF for the types of the translocation cases are expressed. In this regard, the contents of the DF columns may be of translocations in a vicinity of BP regions.

The lines of CF contain the CF presence information explained in conjunction with FIG. 6.

Each column of the lines of CF expresses CF for the translocation case type indicated by the top column. In the first chromosome line, the presence or absence of CF in the first chromosome is denoted. The mark 'O' indicates the presence of DF in the first chromosomes whereas the mark 'X' denotes the absence of DF in the first chromosomes. In the second chromosome line of CF, the presence or absence of CF in the second chromosome is denoted. The mark 'O' indicates the presence of DF in the second chromosomes whereas the mark 'X' denotes the absence of DF in the second chromosomes.

Because CF is absent in the first chromosomes of the translocation case of type (b), the column of type (b) in the first chromosome line is marked with 'O'. On the other hand, the mark 'X' of the column of type (b) in the second chromosome line accounts for the absence of CF in the second chromosomes of the translocation case of type (b). Such marks may be given to translocations cases of other types, and the same descriptions are omitted.

For example, a translocation case in which CF is present in the first chromosome but absent in the second chromosome may include the translocation case of type (b) and the translocation case of type (e). Within the range of the translocation case in which CF is absent in the first chromosomes, but present in the second chromosome, the translocation cases of type (f) and type (g) may fall. The presence of CF in both the first and the second chromosomes accounts for the translocation cases of types (a), (c), and (d).

In step (630), as described in FIG. 6, the detection unit 420 may produce CF information indicating that CF is present in both the first and the second chromosomes. For this, the detection unit 420 in step (643) may select a translocation case in which 'O' is given to both the first chromosome line and the second chromosome line. That is to say, the detection unit 420 in step (643) may select the translocation case of type (a), type (c) or type (d) as at least one translocation case corresponding to the CF information from among all or a part of the possible multiple translocation cases. Similar determination and selection may be applied to other DF information. The same descriptions are omitted of the determination and selection.

According to the steps (610), (620), (630), (640), (641), (642) and (643) described in conjunction with FIG. 6 and the table of FIG. 7, an illustrative method for detecting a translocation may be conducted as follows.

When the DF information produced in step (610) indicates the absence of '5 to 3' BP and the presence of '3 to 5' BP while the CF information produced in step (630) means the presence of a CF in each of the first and the second chromosomes, at least one translocation case selected in step (640) may be a translocation case of type (a) in which a translocation exists in one of the second paired chromosomes, but not in any of the first paired chromosomes.

When it is determined in step (620) that the ploidy in a vicinity of a BP region on the first chromosomes is two times the mean RD and the ploidy in a vicinity of a BP region on the second chromosomes is zero, at least one translocation case selected in step (640) may be a translocation case of type (b) in which a translocation exists in both of the second paired chromosomes, but not in any of the first paired chromosomes.

When the DF information produced in step (610) indicates the presence of '5 to 3' BP and the absence of '3 to 5' BP while the CF information produced in step (630) teaches the presence of CF in each of the first and the second chromosomes, at least one translocation case selected in step (640) may be a translocation case of type (c) in which a translocation is present in one of the first paired chromosomes and absent in both of the second paired chromosomes.

When the DF information produced in step (610) explains the presence of both '5 to 3' BP and '3 to 5' BP while the CF information produced in step (630) indicates the presence of CF in each of the first and the second chromosomes, at least one translocation case selected in step (640) may be a translocation case of type (d) in which a translocation is present in one of the first paired chromosomes and in one of the second paired chromosomes.

When the DF information produced in step (610) explains the presence of both '5 to 3' BP and '3 to 5' BP while the CF information produced in step (630) indicates the presence of CF in the first chromosomes and the absence of CF in the second chromosomes, at least one translocation case selected in step (640) may be a translocation case of type (e) in which a translocation is present in one of the first paired chromosomes and in both of the second paired chromosomes.

When it is determined in step (620) that the ploidy in a vicinity of a BP region on the first chromosomes is zero and the ploidy in a vicinity of a BP region on the second chromosomes is two times the mean RD, at least one translocation case selected in step (640) may be a translocation case of type (f) in which a translocation exists in both of the first paired chromosomes, but not in any of the second paired chromosomes.

When the DF information produced in step (610) explains the presence of both '5 to 3' BP and '3 to 5' BP while the CF information produced in step (630) indicates the absence of CF in each of the first chromosomes and the presence of CF in the second chromosomes, at least one translocation case selected in step (640) may be a translocation case of type (g) in which a translocation is present in both of the first paired chromosomes and in one of the second paired chromosomes.

When the DF information produced in step (610) explains the presence of both '5 to 3' BP and '3 to 5' BP while the CF information produced in step (630) indicates the absence of CF in both the first and the second chromosomes, at least one translocation case selected in step (640) may be a translocation case of type (h) in which a translocation is present in both of the first paired chromosomes and in both of the second paired chromosomes.

FIG. 8 shows results of a BP analysis test in accordance with an embodiment of the present invention.

The validity of the translocation detecting method described above may be proven by an experiment using simulation NGS data. In order to produce simulation data, the currently used reference sequence hg19 may be employed, with the respective selection of chr16 and chr20 as the first chromosome and the second chromosome therefrom.

From among the possible multiple translocation cases described above, one translocation case may be selected, after which a sample sequence may be produced, followed by simulation NGS data. The simulation NGS data may be simulation paired-end read fragments. The BAM that is an input data for translocation analysis can be acquired through the read sequence alignment of the simulation NGS data.

FIG. 8 shows experimental results of a translocation case of type (a). To begin with, '3 to 5' BP was detected by BP analysis. The positions of BP on 'chr16' and 'chr20' may be '72280000' and '50420000', respectively. Since the detected BP is '3 to 5' BP, the detected translocation case may be type (a) or type (b).

Figure 9A:
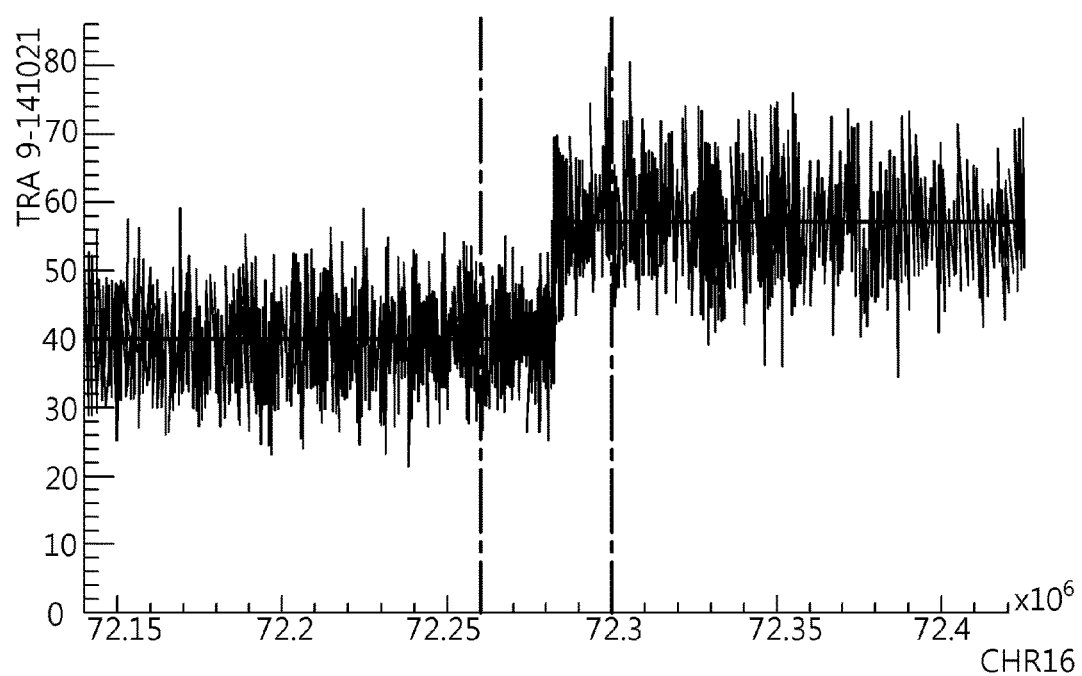
FIG. 9a shows experimental data of RD analysis for 'chr16'.
Figure 9B:
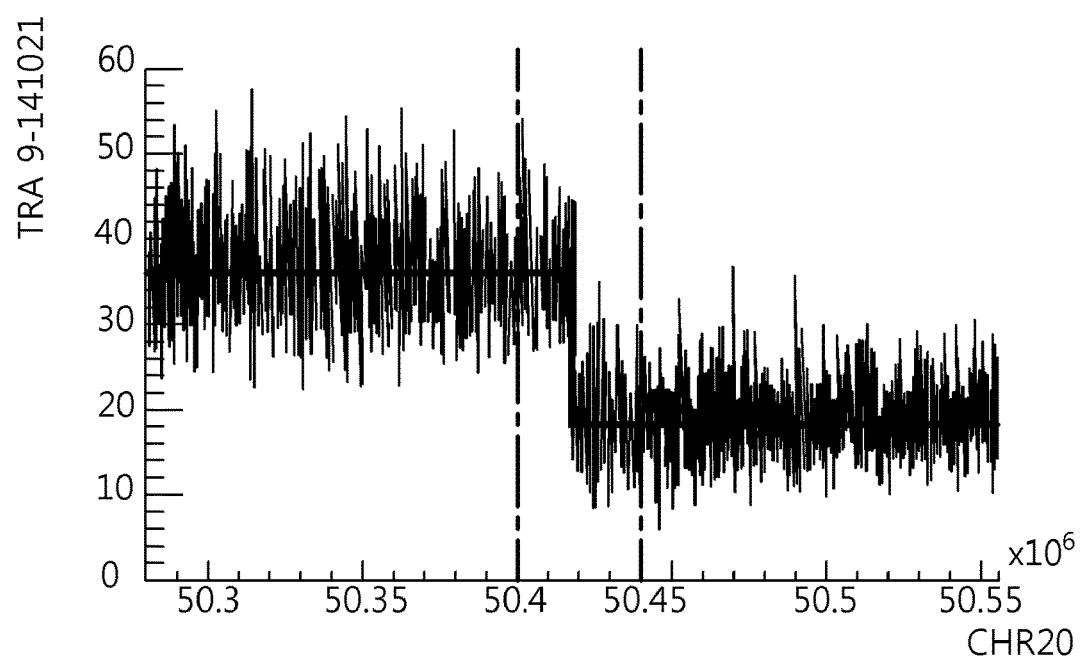
FIG. 9b shows experimental data of RD analysis for 'chr20'.

FIGS. 9a and 9b show experimental results of RD analysis in accordance with an embodiment of the present invention.

FIG. 9a shows experimental data of RD analysis for 'chr16'.

FIG. 9b shows experimental data of RD analysis for 'chr20'.

A combination of the RD analysis result with the experimental results of FIG. 8 teaches that the ploidy is '×1.5' for 'chr16' and '×0.5' for 'chr20'. From the two translocation cases of type (a) and type (b), hence, filtering can remove the translocation of type (b).

FIGS. 9a and 9b may be a result of capturing using a tool CNVnator (Abyzov et al. 2011)

[Reference] Abyzov, A., Urban, A. E., Snyder, M., Gerstein, M., 2011. CNVnator: An approach to discover, genotype, and characterize typical and atypical CNVs from family and population genome sequencing. Genome Research 21, 974-984.

Figure 10A:
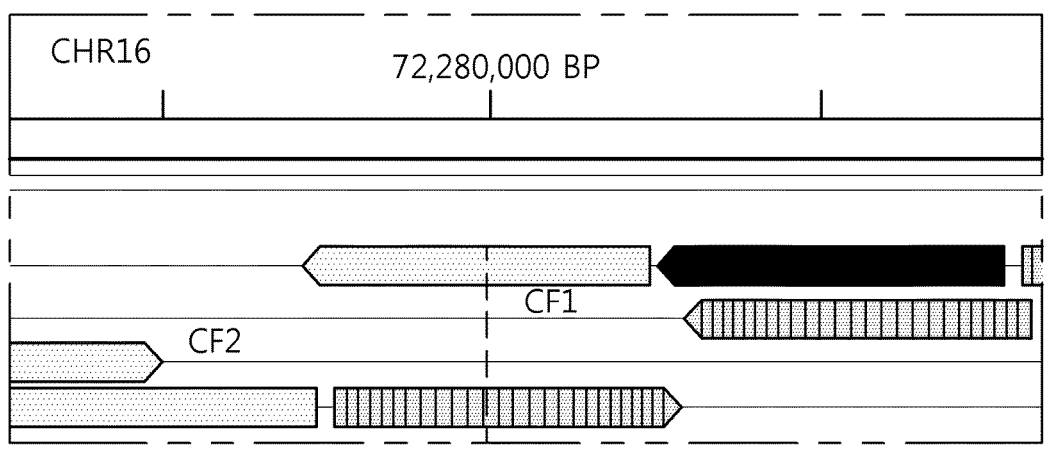
FIG. 10a shows experimental data of CF analysis for 'chr16'.
Figure 10B:
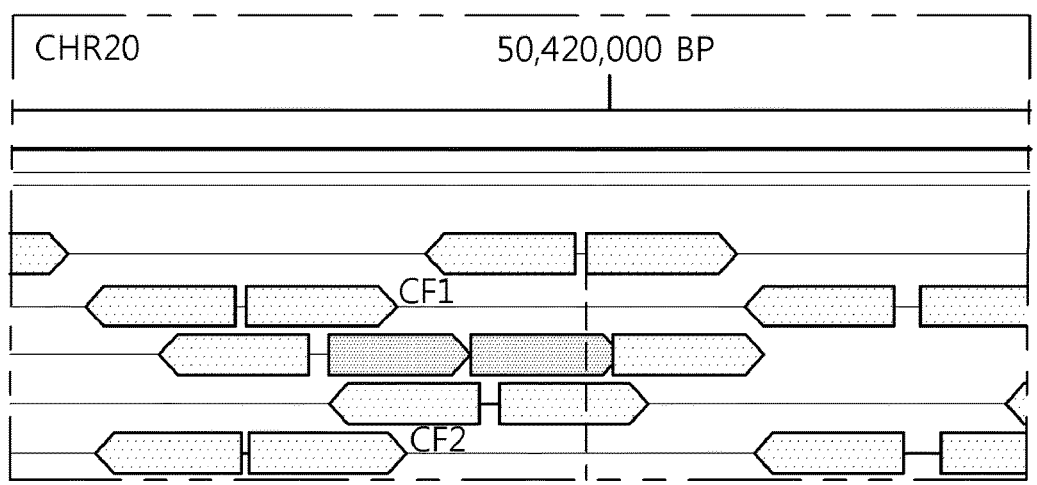
FIG. 10b shows experimental data of CF analysis for 'chr20'.

FIGS. 10a and 10b show experimental results of CF analysis in accordance with an embodiment of the present invention.

FIG. 10a shows experimental data of CF analysis for 'chr16'.

FIG. 10b shows experimental data of CF analysis for 'chr20'.

Results of CF analysis for both 'chr16' and 'chr20' may indicate the presence of CF in a vicinity of BP on both 'chr16' and 'chr20'. The CF indicated by the experimental results may be coincident with that of the translocation case of type (a). Therefore, all the results of BP analysis, RD experiments, and CF experiments may be proven accurate.

In addition to the translocation case of type (a), other possible multiple translocation cases may be subjected to the analyses and experiments described in conjunction with FIGS. 8 to 10*b* to produce data. It was found that effective translocation detection could be achieved for all the translocation cases. These results may be attributed to difference in BP, RD and CF patterns from one of the possible multiple translocation cases to another.

The method for detecting a translocation described above can analyze a translocation, which is one of important variations present in human genes, on the basis of NGS data. The translocation detecting method is described to take advantage of NGS data in detecting a translocation on a gene. In the method suggested herein, CF information on BP regions of SV as well as PE information, SR information and RD information can be utilized for detecting a translocation. Using the CF information, the translocation detecting method can restore a ploidy state of BP, which cannot be attained only with PE information and SR information. By restoring the ploidy state, the translocation detecting method can reveal whether a translocation is present in either or both of two paired chromosomes. In addition, the translocation detecting method may be applicable to the detection of translocations whether they are copy number neutral or variable.

In the above-mentioned embodiments, translocation cases that are possible are all explained, and translocation detection according to the analysis of BP, RD and CF patterns for each translocation case is proposed. Further, experiments with simulation NGS data demonstrated the validity of the proposed translocation detecting method.

Figure 11:
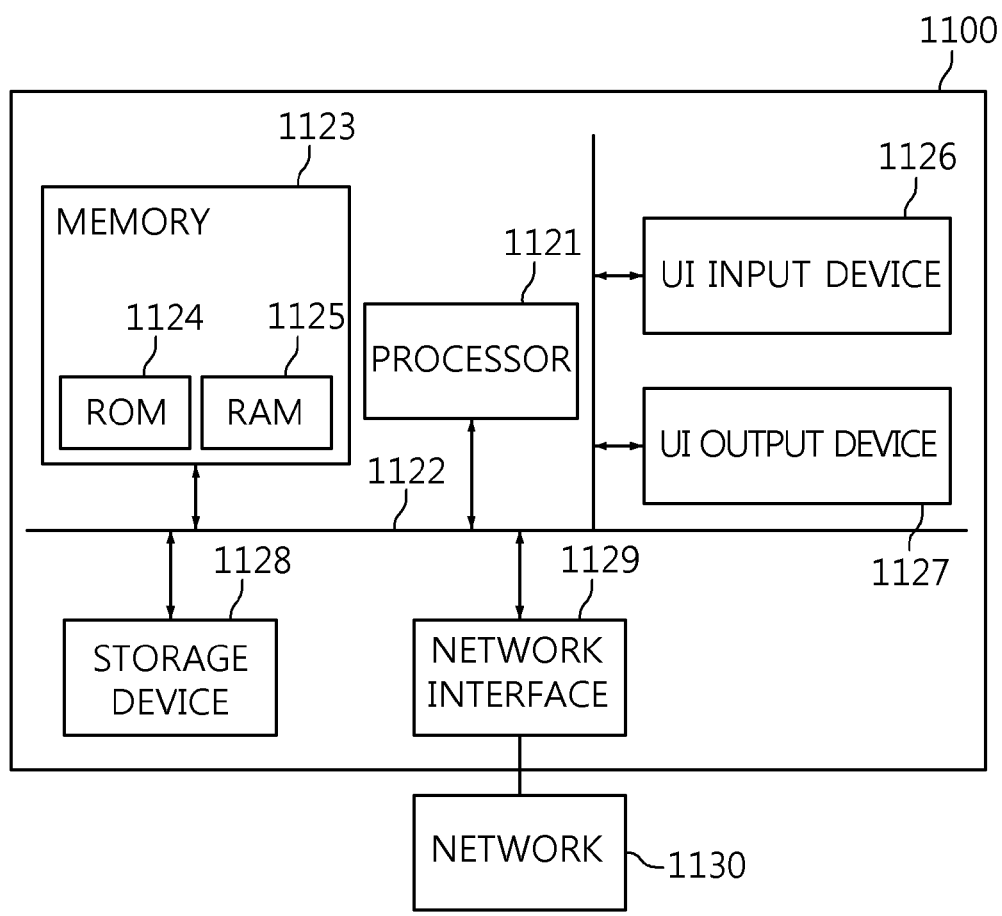
FIG. 11 is a schematic structural view of an electronic apparatus as an embodiment of the apparatus for detecting a translocation.

FIG. 11 is a schematic structural view of an electronic apparatus as an embodiment of the apparatus for detecting a translocation.

The apparatus 400 for detecting a translocation can be embodied by the electronic apparatus 1100 shown in FIG. 11.

The performance of the translocation detecting apparatus 400 may be conducted in a computer system comprising a record medium that can be read by a computer. As can be seen in FIG. 11, the electronic apparatus 1100 may comprise at least one processor that communicates with a network through a BUS 1122, a memory 1123, a user interface (UI) input device 1126, a UI output device 1127, and a storage device 1128. Also, the electronic apparatus 1100 may further comprise a network interface 1129 connected to the network 1130. The processor 1121 may be a semiconductor device configured to execute processing instructions stored in a central processing unit (CPU) or the memory 1123 or the storage device 1128. The memory 1123 and the storage device 1128 may be various volatile or non-volatile storage media. For example, the memory may include ROM 1124 or RAM 1125.

At least one module of the translocation detecting apparatus 400 may be stored in the memory or may be configured to be executed by the at least one processor 1121. A function relevant to the remote communication of the data or information of the translocation detecting apparatus 400 may be executed through a network interface 1129. Herein, the at least one module may include at least a part of the input unit 410, the detection unit 420, and the output unit 430.

In addition, embodiments of the present invention further relate to computer readable media or computer program products that include program instructions, data files, and/or data structures for performing various computer-implemented operations. The media and program instructions may be those specially designed and constructed for the purposes of the present invention, or they may be of the kind well known and available to those having skill in the computer software arts. Examples of computer-readable media include, but are not limited to, magnetic media such as hard disks, floppy disks, and magnetic tape; optical media such as CD-ROM, or DVD disks; magneto-optical media such as floptical disks; and hardware devices that are specially configured to store and perform program instructions, such as ROM, RAM, and flash memories. Examples of program instructions include both machine code, such as produced by a compiler, and files containing higher level code that may be executed by the computer using an interpreter. The described hardware devices may be configured to act as one or more software modules in order to perform the operation of the embodiment, and vice versa.

As described hitherto, a method and apparatus is provided for effectively detecting a translocation by genome analysis.

A method and apparatus is for analyzing a translocation, using information about a concordant fragment present in a break point region of structural variation.

A method and apparatus is provided for determining the presence of a translocation in either or both of paired chromosomes by restoring a ploidy state of a break point.

A method and apparatus is provided for detecting a translocation that is copy number variable or copy number neutral.

As described above, optimal embodiments of the present invention have been disclosed in the drawings and the specification. Although specific terms have been used in the present specification, these are merely intended to describe the present invention and are not intended to limit the meanings thereof or the scope of the present invention described in the accompanying claims. Therefore, those skilled in the art will appreciate that various modifications and other equivalent embodiments are possible from the embodiments. Therefore, the technical scope of the present invention should be defined by the technical spirit of the claims.

What is claimed is:

1. A method for detecting a translocation, comprising:
acquiring a binary version of sequence alignment/map (BAM) for a first pair of chromosomes and a second pair of chromosomes; and
detecting, using the BAM, a translocation generated in at least one chromosome by selecting at least one translocation case from among multiple translocation cases, including:
determining, using the BAM, at least one Break Point (BP) of the pairs of chromosomes, each of the at least one BP corresponding to respective point where a translocation has occurred between the first and second pairs of chromosomes, including determining, using the BAM, Discordant Fragment (DF) information corresponding to the at least one BP;
determining, using the BAM, a Read Depth (RD) of a first region in the first pair of chromosomes, a RD of a second region in the second pair of chromosomes, an average RD of the BAM, and concordant fragment (CF) information of the second region indicating the presence of CFs for the second region;
selecting a first translocation case when the RD of the first region is 1.5 times the average RD, the RD of the second region is 0.5 times the average RD, the DF information indicates the presence of DFs in the second pair of chromosomes, and CFs are present for the first region and the second region; and selecting a second translocation case when the RD of the first region is 2.0 times the average RD, the RD of the second region is zero, the DF information indicates the presence of DFs in the second pair of chromosomes, and CFs are present for the first region and absent for the second region, wherein the first translocation case corresponds to a single translocation from the first pair of chromosomes to a first chromosome of the second pair of chromosomes, and wherein the second translocation case corresponds to first and second translocations from the first pair of chromosomes to the first chromosome and a second chromosome, respectively, of the second pair of chromosomes.

2. The method of claim 1, wherein determining the DF information comprises:

analyzing the BP using paired end (PE) information and split-read (SR) information of the BAM to produce the DF information.

3. The method of claim 1, wherein the DF information includes information about the following: a ploidy in a region on the first pair of chromosomes, a ploidy in a region on the second pair of chromosomes, and information about CF presence, and the DF information shows at least one BP present in the first pair of chromosomes or the second pair of chromosomes.

4. The method of claim 1, detecting the translocation further including:

determining, using the BAM, CF information of the first region indicating the presence of CF for the first region;

selecting a third translocation case when the RD of the second region is 1.5 times the average RD, the RD of the first region is 0.5 times the average RD, the DF information indicates the presence of DFs in the first pair of chromosomes, and CF is present for the first region and the second region, wherein the third translocation case corresponds to a single translocation from the second pair of chromosomes to a first chromosome of the first pair of chromosomes.

5. The method of claim 4, detecting the translocation further including:

selecting a fourth translocation case when the RD of the first region is 1.0 times the average RD, the RD of the second region is 1.0 times the average RD, the DF information indicates the presence of DFs in the first pair of chromosomes and in the second pair of chromosomes, and CF is present for the first region and for the second region, wherein the fourth translocation case corresponds to a first translocation from the second pair of chromosomes to the first pair of chromosomes and a second translocation from the first pair of chromosomes to the second pair of chromosomes.

6. The method of claim 4, detecting the translocation further including:

selecting a fifth translocation case when the RD of the first region is 1.5 times the average RD, the RD of the second region is 0.5 times the average RD, the DF information indicates the presence of DFs in the first pair of chromosomes and in the second pair of chromosomes, and CF is present for the first region and absent for the second region, wherein the fifth translocation case corresponds to first and second translocations from the first pair of chromosomes to the first chromosome and a second chromosome, respectively, of the second pair of chromosomes and a single third translocation from the second pair of chromosomes to a first chromosome of the first pair of chromosomes.

7. The method of claim 4, detecting the translocation further including:

selecting a sixth translocation case when the RD of the first region is zero, the RD of the second region is 2.0 times the average RD, the DF information indicates the presence of DFs in the first pair of chromosomes, and CF is absent for the first region and present for the second region, wherein the sixth translocation case corresponds to first and second translocations from the second pair of chromosomes to the first chromosome and a second chromosome, respectively, of the first pair of chromosomes.

8. The method of claim 4, detecting the translocation further including:

selecting a seventh translocation case when the RD of the first region is 0.5 times the average RD, the RD of the second region is 1.5 times the average RD, the DF information indicates the presence of DFs in the first pair of chromosomes and in the second pair of chromosomes, and CF is absent for the first region and present for the second region, wherein the seventh translocation case corresponds to first and second translocations from the second pair of chromosomes to the first chromosome and a second chromosome, respectively, of the first pair of chromosomes, and a single third translocation from the first pair of chromosomes to a first chromosome of the second pair of chromosomes.

9. The method of claim 4, detecting the translocation further including:

selecting an eighth translocation case when the RD of the first region is 1.0 times the average RD, the RD of the second region is 1.0 times the average RD, the DF information indicates the presence of DFs in the first pair of chromosomes and in the second pair of chromosomes, and CF is absent for the first region and the second region, wherein the eighth translocation case corresponds to first and second translocations from the second pair of chromosomes to the first chromosome and a second chromosome, respectively, of the first pair of chromosomes and third and fourth translocations from the first pair of chromosomes to a first chromosome and a second chromosome, respectively, of the second pair of chromosomes.

10. An apparatus for detecting translocation, comprising:
a processor configured to:
acquire a binary version of sequence alignment/map (BAM) for a first pair of chromosomes and a second pair of chromosomes, and
detect, using the BAM, a translocation generated in at least one chromosome by selecting at least one translocation case from among multiple translocation cases, wherein the processor is configured to:
determine, using the BAM, at least one Break Point (BP) of the pairs of chromosomes, each of the at least one BP corresponding to respective point where a translocation has occurred between the first and second pairs of chromosomes, including determining, using the BAM, Discordant Fragment (DF) information corresponding to the at least one BP;

determine, using the BAM, a Read Depth (RD) of a first region in the first pair of chromosomes, a RD of a second region in the second pair of chromosomes, an average RD of the BAM, and concordant fragment (CF) information of the second region indicating the presence of CF for the second region;

select a first translocation case when the RD of the first region is 1.5 times the average RD, the RD of the second region is 0.5 times the average RD, the DF information indicates the presence of DFs in the second pair of chromosomes, and CF is present for the first region and the second region; and select a second translocation case when the RD of the first region is 2.0 times the average RD, the RD of the second region is zero, the DF information indicates the presence of DFs in the second pair of chromosomes, and CF is present for the first region and absent for the second region, wherein the first translocation case corresponds to a single translocation from the first pair of chromosomes to a first chromosome of the second pair of chromosomes, and wherein the second translocation case corresponds to first and second translocations from the first pair of chromosomes to the first chromosome and a second chromosome, respectively, of the second pair of chromosomes.

11. The apparatus of claim 10, wherein the processor is configured to:

determine, using the BAM, CF information of the first region indicating the presence of CF for the first region; and select a third translocation case when the RD of the second region is 1.5 times the average RD, the RD of the first region is 0.5 times the average RD, the DF information indicates the presence of DFs in the first pair of chromosomes, and CF is present for the first region and for the second region, wherein the third translocation case corresponds to a single translocation from the second pair of chromosomes to a first chromosome of the first pair of chromosomes.

12. The apparatus of claim 11, wherein the processor is configured to:

select a fourth translocation case when the RD of the first region is 1.0 times the average RD, the RD of the second region is 1.0 times the average RD, the DF information indicates the presence of DFs in the first pair of chromosomes and in the second pair of chromosomes, and CF is present for the first region and for the second region, wherein the fourth translocation case corresponds to a first translocation from the second pair of chromosomes to the first pair of chromosomes and a second translocation from the first pair of chromosomes to the second pair of chromosomes.

13. The apparatus of claim 11, wherein the processor is configured to:

select a fifth translocation case when the RD of the first region is 1.5 times the average RD, the RD of the second region is 0.5 times the average RD, the DF information indicates the presence of DFs in the first pair of chromosomes and in the second pair of chromosomes, and CF is present for the first region and absent for the second region, wherein the fifth translocation case corresponds to first and second translocations from the first pair of chromosomes to the first chromosome and a second chromosome, respectively, of the second pair of chromosomes and a single third translocation from the second pair of chromosomes to a first chromosome of the first pair of chromosomes.

14. The apparatus of claim 11, wherein the processor is configured to:

select a sixth translocation case when the RD of the first region is zero, the RD of the second region is 2.0 times the average RD, the DF information indicates the presence of DFs in the first pair of chromosomes, and CF is absent for the first region and present for the second region, wherein the sixth translocation case corresponds to first and second translocations from the second pair of chromosomes to the first chromosome and a second chromosome, respectively, of the first pair of chromosomes.

15. The apparatus of claim 11, wherein the processor is configured to:

select a seventh translocation case when the RD of the first region is 0.5 times the average RD, the RD of the second region is 1.5 times the average RD, the DF information indicates the presence of DFs in the first pair of chromosomes and in the second pair of chromosomes, and CF is absent for the first region and present for the second region, wherein the seventh translocation case corresponds to first and second translocations from the second pair of chromosomes to the first chromosome and a second chromosome, respectively, of the first pair of chromosomes, and a single third translocation from the first pair of chromosomes to a first chromosome of the second pair of chromosomes.

16. The apparatus of claim 11, wherein the processor is configured to:

select an eighth translocation case when the RD of the first region is 1.0 times the average RD, the RD of the second region is 1.0 times the average RD, the DF information indicates the presence of DFs in the first pair of chromosomes and in the second pair of chromosomes, and CF is absent for the first region and the second region, wherein the eighth translocation case corresponds to first and second translocations from the second pair of chromosomes to the first chromosome and a second chromosome, respectively, of the first pair of chromosomes and third and fourth translocations from the first pair of chromosomes to a first chromosome and a second chromosome, respectively, of the second pair of chromosomes.

* * * * *